(12) United States Patent
Neal et al.

(10) Patent No.: US 6,706,245 B2
(45) Date of Patent: Mar. 16, 2004

(54) THREE STAGE NEEDLE FOR USE WITH AN AUTOSAMPLER

(75) Inventors: David M. Neal, Shawnee, KS (US); Edward K. Price, Liberty Township, OH (US); Harry W. Schmidt, Fairfield, OH (US)

(73) Assignee: Teledyne Tekmar Company, Mason, OH (US)

( * ) Notice: Subject to any disclaimer, the term of this patent is extended or adjusted under 35 U.S.C. 154(b) by 393 days.

(21) Appl. No.: 09/803,407

(22) Filed: Mar. 9, 2001

(65) Prior Publication Data

US 2002/0006360 A1 Jan. 17, 2002

Related U.S. Application Data

(60) Provisional application No. 60/188,269, filed on Mar. 10, 2000, and provisional application No. 60/188,665, filed on Mar. 11, 2000.

(51) Int. Cl.$^7$ ................................................ B01L 3/02
(52) U.S. Cl. .................. 422/100; 73/863.32; 73/864; 73/864.01; 73/864.11; 73/864.74
(58) Field of Search ................... 422/100; 73/863.32, 73/864, 864.01, 864.11, 864.74; 604/239

(56) References Cited

U.S. PATENT DOCUMENTS

| | | | | |
|---|---|---|---|---|
| 3,521,715 A | * | 7/1970 | Krutein ........................ | 175/5 |
| 4,038,875 A | * | 8/1977 | Walkotten ................. | 73/863.11 |
| 4,310,057 A | * | 1/1982 | Brame ......................... | 175/21 |
| 5,227,139 A | * | 7/1993 | Wong ........................... | 422/103 |
| 5,945,070 A | * | 8/1999 | Kath et al. ................... | 422/101 |
| 5,948,360 A | | 9/1999 | Rao et al. | |
| 6,042,787 A | * | 3/2000 | Pawliszyn ..................... | 422/69 |
| 6,180,410 B1 | * | 1/2001 | Gerstel et al. ................. | 436/54 |
| 6,447,728 B1 | * | 9/2002 | Wilmes et al. .............. | 422/100 |
| 2002/0094304 A1 | * | 7/2002 | Yang et al. .................. | 422/100 |
| 2002/0168778 A1 | * | 11/2002 | Andrien et al. ............. | 436/173 |
| 2003/0003596 A1 | * | 1/2003 | Pawliszyn ................... | 436/178 |

OTHER PUBLICATIONS

U.S. patent application Ser. No. 09/803,405 filed Mar. 9, 2001.
U.S. patent application Ser. No. 09/803,412 filed Mar. 9, 2001.
U.S. patent application Ser. No. 09/803,414 filed Mar. 9, 2001.
U.S. patent application Ser. No. 09/803,721 filed Mar. 9, 2001.

* cited by examiner

*Primary Examiner*—Jill Warden
*Assistant Examiner*—Brian R. Gordon
(74) *Attorney, Agent, or Firm*—Kirkpatrick & Lockhart LLP

(57) ABSTRACT

A three stage needle for use with a sampling station of an autosampler to facilitate gas and liquid extractions and injections. The needle includes a bottom stage, a middle stage, and a top stage. Each of the stages of the needle includes at least one aperture used to extract gas or liquid from a specimen or perform an injection. In addition, each of the stages can be placed in fluidic communication with the sampling station to facilitate the desired extraction or injection.

17 Claims, 9 Drawing Sheets

THREE STAGE NEEDLE FOR USE WITH AN AUTOSAMPLER

CROSS REFERENCE TO RELATED APPLICATION

This application claims the benefit of U.S. Provisional Patent Application No. 60/188,269, entitled "WATER AND SOIL AUTOSAMPLER," filed on Mar. 10, 2000 and U.S. Provisional Patent Application No. 60/188,665, entitled "IMPROVED VIAL HANDLING SYSTEM," filed Mar. 11, 2000.

FIELD OF THE INVENTION

The present invention relates to autosamplers, which are mechanical device., that can be used to extract samples from specimens, prepare the samples for analysis, and provide the samples to an analytical instrument. More particularly, the present invention relates to a needle for use with a sampling station of an autosampler to facilitate performing the above-described tasks.

BACKGROUND OF THE INVENTION

Autosamplers are generally used to extract gas and liquid samples from specimens stored in containers such as vials. Once extracted, the sample can be transferred to an analytical instrument for analysis, such as the 3100 Concentrator sold by Tekmar-Dohrmann, Cincinnati, Ohio, U.S.A.

Autosamplers typically use separate sampling stations for extracting liquid and gas samples. One example of such an autosampler is described in U.S. Pat. No. 5,948,360 to Rao et al. and assigned to Tekmar Company, Cincinnati, Ohio, U.S.A. Liquid sampling typically involves extracting a known quantity of liquid from the vial that is presented to the sampling station of the autosampler, adding a standard to the sample, and transferring the sample and the standard to an analytical device. Under certain situations, the specimen must be diluted by a technician by injecting the specimen with a specified volume of methanol or a water-based solution prior to sampling. The extracted sample or methanol extract is then diluted with water prior to analysis by the analytical device.

Gas headspace extraction generally involves injecting the specimen with a solvent, such as water, agitating the specimen, and purging the specimen with a gas. Some autosamplers are adapted to perform static headspace extraction while others are adapted to perform dynamic headspace extraction. In static headspace extraction, the specimen is purged from above the specimen and the headspace is removed and transferred to the analytical device. In dynamic headspace extraction, the specimen is purged from underneath the specimen and the head space is removed and transferred to the analytical instrument. Autosamplers that are capable of performing the above sample extraction procedures include the Precept II and the 7000 HT autosamplers sold by Tekmar-Dohrmann, Cincinnati, Ohio, U.S.A.

The processes of extracting liquid and gas samples using current sampling stations require a technician to perform the standard injections, the methanol dilutions, and other process steps. As a result, in addition to being time consuming, these procedures carry the likelihood of inconsistent injections and a high potential for error. With gas extraction, such as that used for soil analysis, the vial must remain sealed to comply with EPA method 5035. Further time is lost due to the inability to perform both liquid and gas extractions at a single sampling station or autosampler station.

Therefore, a need exists for a sampling station of an autosampler that is capable of performing both liquid and gas extractions while reducing the reliance upon sample preparation by a technician, and remaining compliant with EPA method 5035. A need also exists for a needle that can facilitate the various extractions and dilutions that can be performed by such a sampling station.

SUMMARY

A three stage needle for use with a sampling station of an autosampler is provided and is adapted to facilitate gas and liquid extractions and injections. The needle includes a bottom stage, a middle stage, and a top stage. Each of the stages of the needle includes at least one aperture used to extract gas or liquid from a specimen or perform an injection. In addition, each of the stages can be placed in fluidic communication with the sampling station to facilitate the desired extraction or injection.

DETAILED DESCRIPTION

Figure 1:
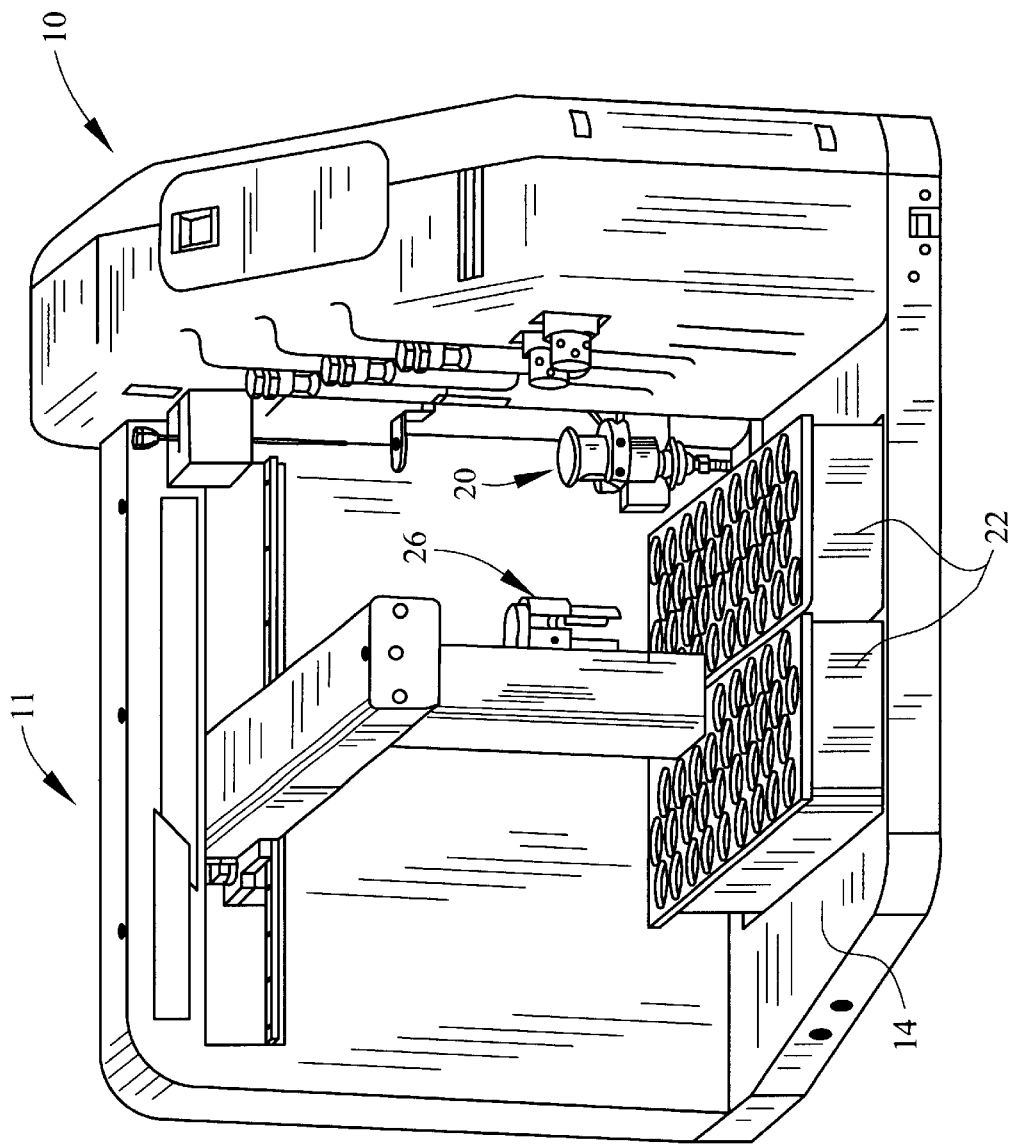
FIG. 1 is a perspective view of an example of an autosampler with which embodiments of the present invention can be used.

FIG. 1. shows a perspective view of an autosampler 10, with which the needle 12 of the present invention can be used. Autosampler 10 can be used to conduct various automated water and soil sampling procedures to extract samples from specimens and deliver the samples to an analytical instrument for analysis. One embodiment of the autosampler 10 includes a base unit 11 that includes a vial storage area 14 and sampling station 20.

Vial storage area 14 includes vial storage racks 22 configured to hold vials 24 and receive vials 24 from vial transporter 26. Alternatively, vial storage racks 22 could be substituted for a vial-carrying rotating carousel (not shown) or other known automated vial advancement device. Vial storage area can also include heating blocks for elevating the temperature of the specimens contained in vials 24 that are stored in racks 22.

Figure 2:
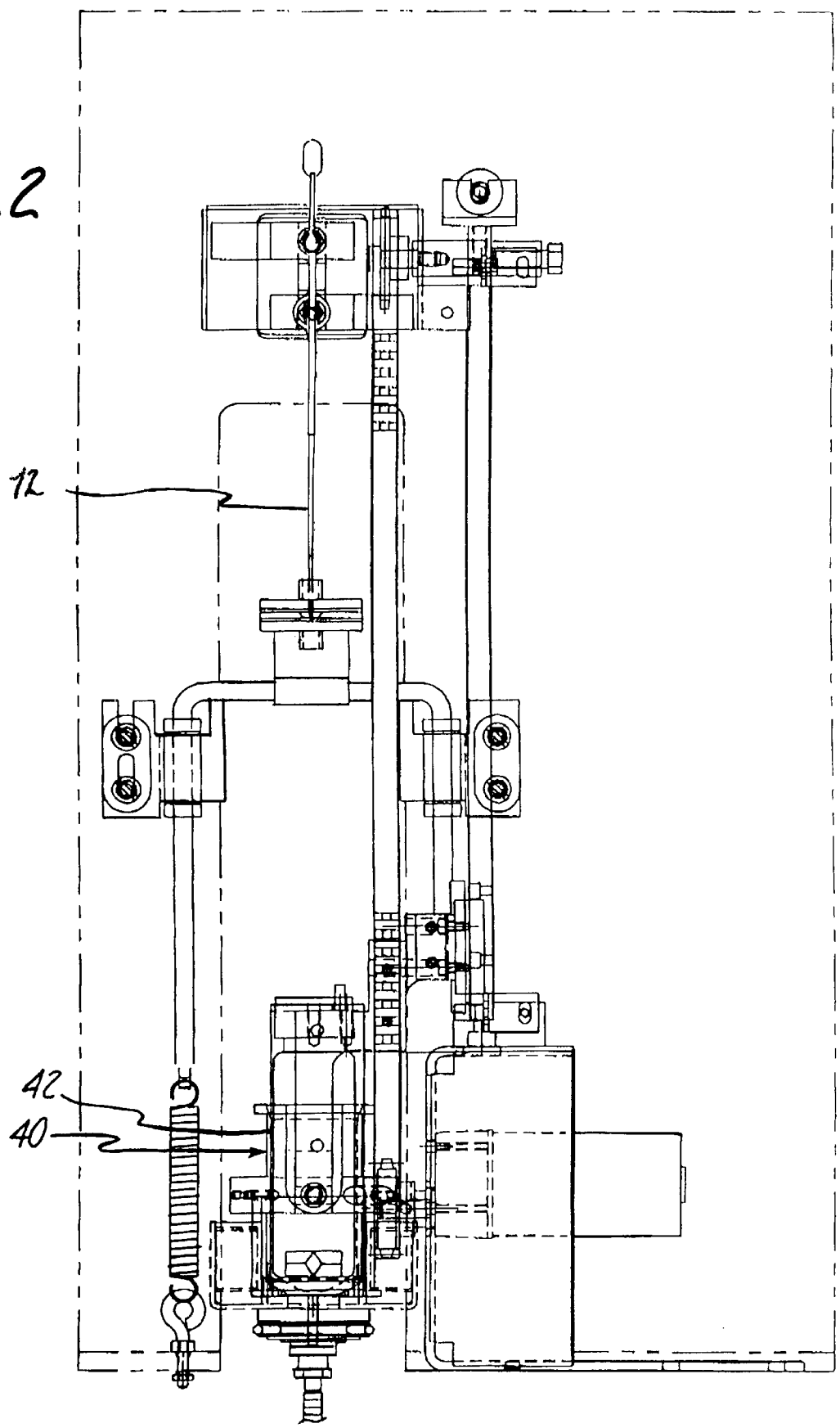
FIG. 2 is a front plan view of a sampling station.
Figure 3:
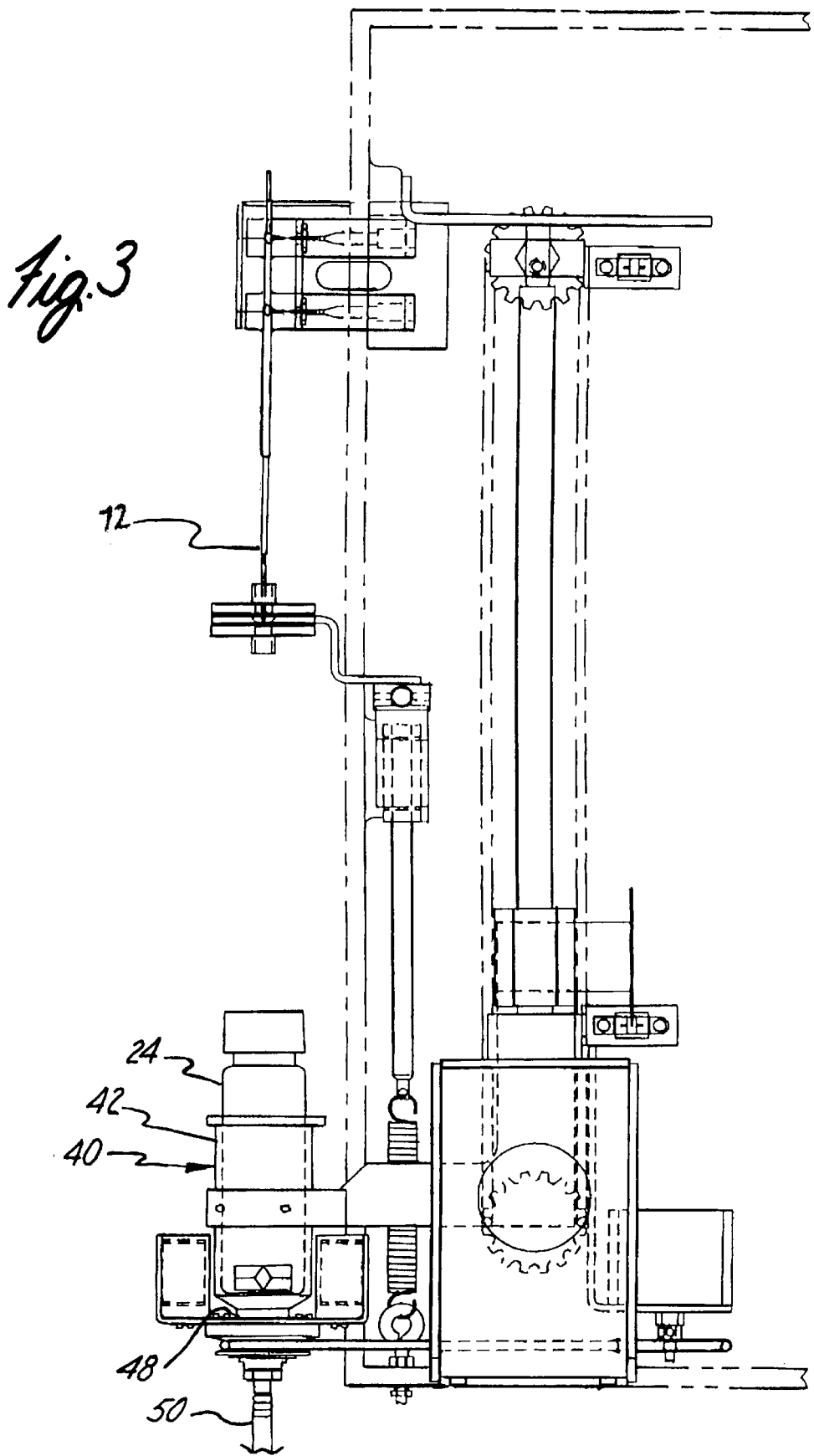
FIG. 3 is a cross-sectional view of a sampling station.

FIGS. 2 and 3 show one embodiment of sampling station 20. A vial holder assembly 40 can be raised or lowered with the assistance of a suitable elevator system, shown in outline in FIGS. 2 and 3. One embodiment of vial holder assembly 40 includes a vial holder cup 42. Vial holder cup 42 can include a drain 48 connected to tubing 50 which delivers the contents of vial holder cup 42 to waste. In addition, vial holder cup 42 can include a heating section for heating the contents of a vial 24. An elevator can raise or lower vial holder cup 42. Sensors can be used to limit the raising and lowering of vial holder cup 42 between a high or raised position, and a lowered position.

Figure 4:
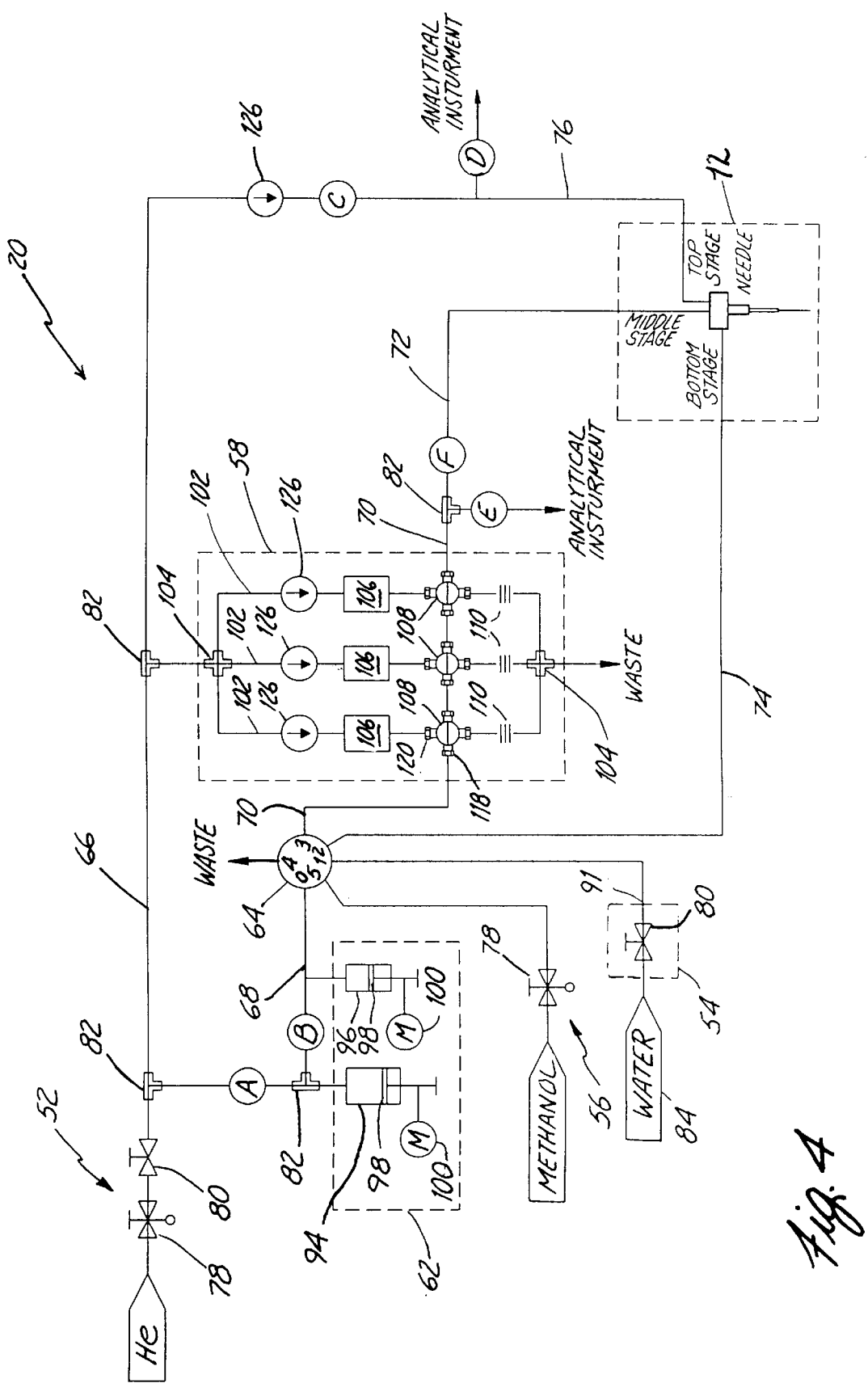
FIG. 4 is a schematic diagram of a sampling station, in accordance with embodiments of the invention.

Sampling station 20 performs various automated sampling procedures on a specimen contained in a vial 24, such as water sampling and headspace gas sampling. FIG. 4 shows a schematic diagram of one embodiment of sampling station 20. Sampling station 20 is generally a fluid circuit that includes a gas/pressure control module 52, a water control module 54, a methanol control module 56, an internal standards system 58, needle 12, and a pump 62. On-off valves A–F and multi-port valve 64 control the flow of fluid through lines 66, 68, 70, 72, 74, and 76. Sampling of a specimen contained in a vial 24 can occur when vial holder assembly 40 of sampling station 18 presents the vial 24 to sampling station 20 by elevating the vial 24 to the raised position causing needle 12 to penetrate the vial 24 and be appropriately positioned for sampling the specimen.

Gas/pressure control module 52 receives a pressurized gas such as helium as shown in FIG. 4. Gas/pressure control module 52 is generally configured to regulate the pressure and flow of gas in sampling station 20 and includes a pressure regulator 78 and a flow controller 80. Pressure regulator 78 regulates the pressure inline 66. Flow controller 80 controls the flow of gas into line 66. Line 66 provides fluid communication between gas/pressure module 52 and internal standards system 58, valve A, and valve C, using T-connectors 82. In one embodiment, gas/pressure module 52 can be used to pressurize an external water reservoir 84 to facilitate delivering water to water control module 54.

Figure 5:
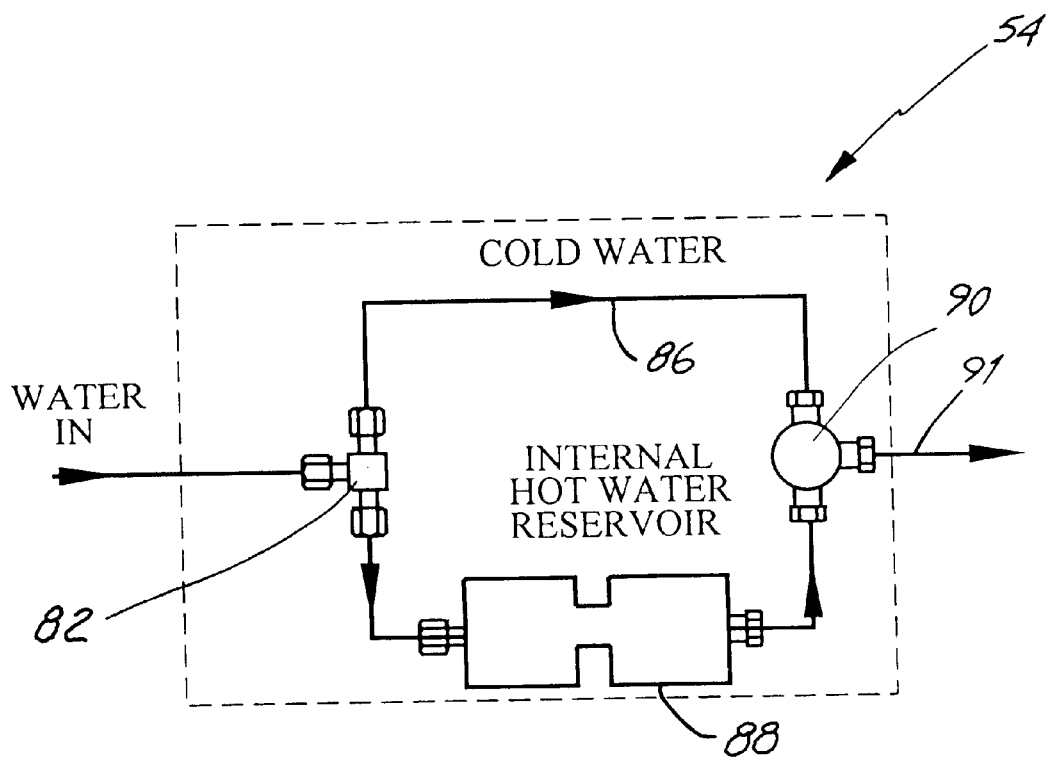
FIG. 5 is a simplified schematic of a water control module in accordance with one embodiment of the invention.

Water control module 54 receives water from external water reservoir 84 and delivers water to port 1 of multi-port valve 64 through valve 80, as shown in FIG. 4. FIG. 5 shows one embodiment of water control module 24 that routes incoming water through a cold water section 86 and a hot water reservoir 88 using a T-connector 82. The hot water reservoir 88 is configured to heat a volume of water to a desired temperature. A three-port valve 90 is configured to selectively regulate the flow of either hot or cold water through outlet 91.

Methanol control module 56 is used to provide methanol for use in methanolic dilutions. Methanol control module 56 receives methanol from an external methanol reservoir 92. Methanol control module 56 is placed in fluid communication with port 5 of multi-port valve 64. The pressure at port 5 of multi-port valve 64 can be controlled using a pressure regulator 78.

Pump 62 is generally configured to extract and distribute known quantities of fluid. One embodiment of pump 62 includes a large syringe 94 and a small syringe 96. Each syringe 94, 96 includes an inner plunger 98 that is driven by an external motor 100. Large syringe 94 is configured to handle large volumes of fluid and small syringe 96 is configured to handle small volumes of fluid. For example, large syringe 94 can have a capacity from 1–25 ml (milliliters) and small syringe 96 can have a capacity from 2.5 $\mu$l–250 $\mu$l (microliters). With this arrangement, large syringe 94 can accurately extract or distribute fluid volumes on the order of 1 ml and small syringe 96 can extract or distribute fluid volumes on the order of 2.5 $\mu$l.

Internal standards system 58 allows for the automated injection of at least one standard into line 70. The standard can be, for example, an internal standard, a calibration standard, a surrogate standard, or a matrix spike. The internal standard is typically methanolic or water-based.

FIG. 4 shows one embodiment of internal standards system 58 that includes one or more internal standard lines 102. Each internal standard line 102 is placed in fluid communication with line 66 using an appropriate connector, such as a cross-connector 104 that is capable of connecting three internal standard lines 102 to line 66. Additional internal standard lines 102 could be added using a suitable connector. Each internal standard line 102 includes a pressurized internal standard vessel 106 containing a volume of standard, a metering valve 108, and a restrictive tubing section 110. Internal standard vessels 106 can contain the same or different standards. A second cross connector 104 connects the restrictive tubing section 110 to waste.

Figure 6:
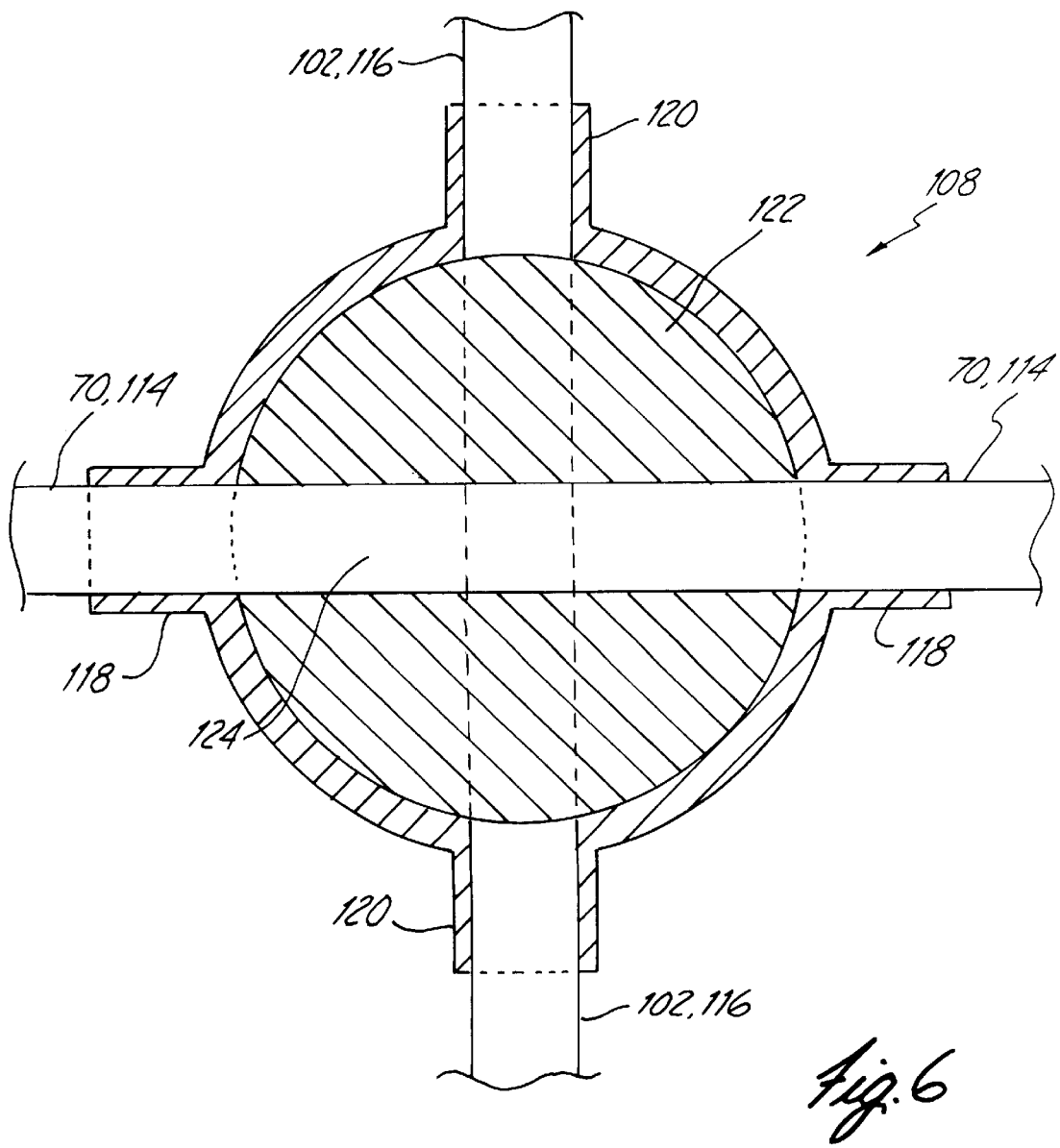
FIG. 6 is a cross-sectional view of a metering valve in accordance with an embodiment of the invention.

Metering valves 108 are generally used to introduce a known volume of standard into line 70 or a first flow path 114, from one of the internal standard lines 102 or a second flow path 116. One embodiment of metering valve 108, shown in FIG. 6, includes a first inlet and outlet 118 inline with first flow path 114 and a second inlet and outlet 120 inline with second flow path 116. A moveable guide member 122 is positioned between the first and second inlet and outlets 118, 120 and includes an internal cavity 124 of a known volume. Valve 108 is defined as being in a "first position" when guide member 122 is positioned to allow fluid communication between first inlet and outlet 118 through internal cavity 124, as shown in FIGS. 4 and 6. Valve 108 is defined as being in a "second position" when guide member 122 is positioned to allow fluid communication between second inlet and outlet 120 through internal cavity 124 shown in dashed lines in FIG. 6. The volume of internal cavity 124 can be sized to be compatible with various calibration standards. In one embodiment, internal cavity 124 has a volume of 5–10 $\mu$l.

Restrictive tubing section 110 is configured to inhibit the flow of standard through cavity 124 of metering valve 108 when metering valve 108 is in the second position by reducing the pressure drop across metering valve 108. Without restrictive tubing section 110 the standard contained within pressurized internal standard vessel 106 would surge through metering valve 108 when in the second position. Restrictive tubing section 110 preferably limits the flow rate of the standard to approximately 30 ml/minute at 10 psi. One embodiment of restrictive tubing section 110 includes conventional tubing having a sufficiently small inner diameter and length to produce the desired pressure drop across restrictive tubing section 110. For example, it has been found that conventional tubing having an inner diameter of 0.010 inch and a length of 8 feet produces a sufficient pressure drop across restrictive tubing section 110 such that the flow of standard through metering valve 108 is reduced to an acceptable rate.

Another embodiment of internal standards system 58 includes check valves 126. Check valves 126 are placed inline with internal standard lines 102 to prevent the back flow of standard, or headspace gas in vessel 106, into other internal standard lines 102 and line 66. A check valve 126 can also be placed inline with line 66 near valve C, as shown in FIG. 4, to prevent the back flow of fluid into line 66 from line 76. One embodiment of the check valves 126 has a 0.5–1 psi crack pressure.

The process of introducing a standard into line 70 includes rotating guide member 122 of metering valve 108 to the second position thereby opening fluid communication between the second inlet and outlet 120 and causing pressurized internal standard vessel 106 to expel standard into internal cavity 124. As the standard flows into internal cavity 124, internal cavity 124 is overfilled with standard with the excess standard being expelled out second outlet 120 of metering valve 108 and into restrictive tubing section 110. Additional materials inline 102 are forced out cross-connector 104 and sent to waste. Once internal cavity 124 is filled with standard, guide member 122 is moved to the first position cutting off fluid communication between the second inlet and outlet 120 and opening fluid communication between the first inlet and outlet 118 of metering valve 108 to introduce the standard contained in internal cavity 124 to line 70 or first flow path 114. In this manner, multiple standard injections can be made to the contents of line 70 simultaneously using multiple internal standard lines 102. In addition, multiple injections of the same standard can be made to line 70 by sweeping the fluid contained in flow path 70 such that each internal cavity 124 of metering valves 108 is clear of standard prior to another injection of standard into line 70. As a result, the volume of standard injected into flow path 70 can be controlled in amounts that are multiples of the volume of internal cavity 124 of metering valves 108. Automation of internal standard system 58 can be achieved through control circuitry (not shown) that is configured to actuate valves 108 between the first and second positions as desired.

Figure 7:
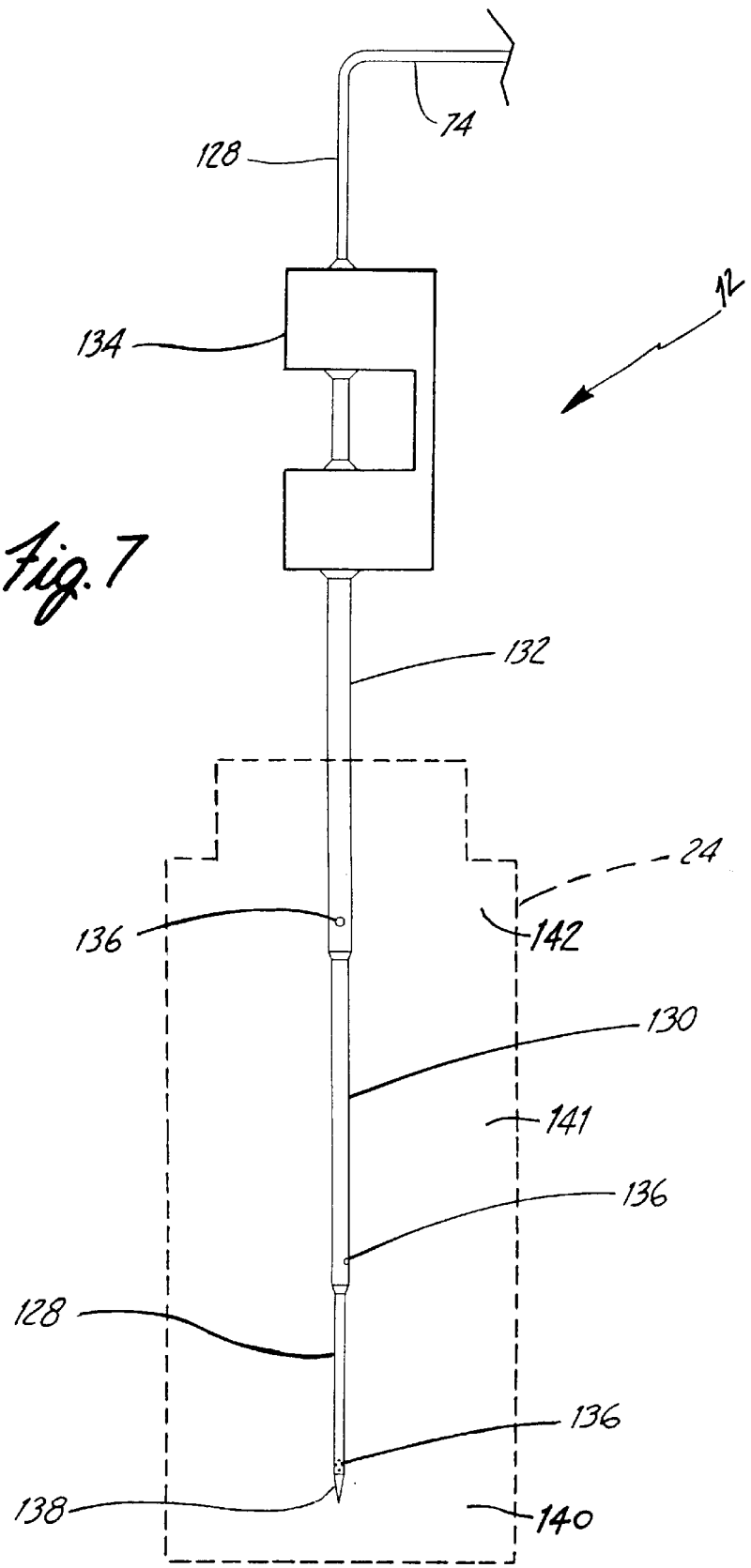
FIG. 7 is a side plan view of a three stage needle in accordance with one embodiment of the invention.

Needle 12 is generally configured to perform fluid and gas headspace extractions and fluid and gas injections on a specimen contained in a vial 24 that is presented to sampling station 20 as mentioned above. FIG. 7 shows one embodiment of needle 12 that includes a bottom stage 128, a middle stage 130, and a top stage 132. Each of the needle stages 128, 130 and 132, are hollow tubing sections that include apertures 136 which allow each of the needle stages 128, 130 and 132, to perform a fluid extraction or injection. In one embodiment, bottom stage 128 includes several small apertures 136 and middle and top stages 130, 132 each include a single large aperture 136, as shown in FIG. 7. In another embodiment, bottom stage 128, middle stage 130, and top stage 132, are substantially concentrically aligned.

Bottom stage 128 generally serves the purpose of extracting fluid from vial 24 for water sampling and purging vial 24 for dynamic headspace gas extraction. Bottom stage 128 includes a pointed tip 138 for piercing a septum and extending into a lower portion 140 of a vial 24 (depicted as a dashed line) that is presented to sampling station 20. Bottom stage 128 is placed in fluid communication with port 2 of multi-port valve 64 through line 74. Middle stage 130 generally serves the purpose of performing fluid injections into vial 24, such as standard injections, and for purging vial 24 during a static headspace extraction. Middle stage 130 extends into a middle portion 141 of vial 24 and is placed in fluid communication with on-off valve F through line 70. Top stage 132 generally serves the purpose of an outlet for gas headspace extractions. Top stage 132 extends into a top portion 142 of vial 24 and is placed in fluid communication with on-off valves C and D through line 76, as shown in FIG. 4.

Another embodiment of needle 12 includes a heating block 134, which generally serves the purpose of preventing gasses flowing in middle stage 130, top stage 132, and/or bottom stage 128 from condensing by heating them. In one embodiment of heating block 134, shown in FIG. 8, bottom stage 128 extends through lower heated portion 143 and upper heated portion 144 of heating block 134. Middle stage 130 extends through lower heated portion 143 and into upper heated portion 144. Middle stage channel 145 connects to middle stage 130 and opens fluid communication between line 70 and middle stage 130 of needle 12. Top stage 132 extends into lower heated portion 143 of heating block 134. Top stage channel 146 provides fluid communication between line 76 and top stage 132 of needle 12. Lower and upper heated portions 143, 144 of heating block 134 can be heated to approximately 100° C., using resistive heating elements or by other methods used in the industry. Lower and upper passages 148, 150, through which the various needle stages pass, can be sealed using a ferrule combination or a collet as is common in the industry.

Figure 9:
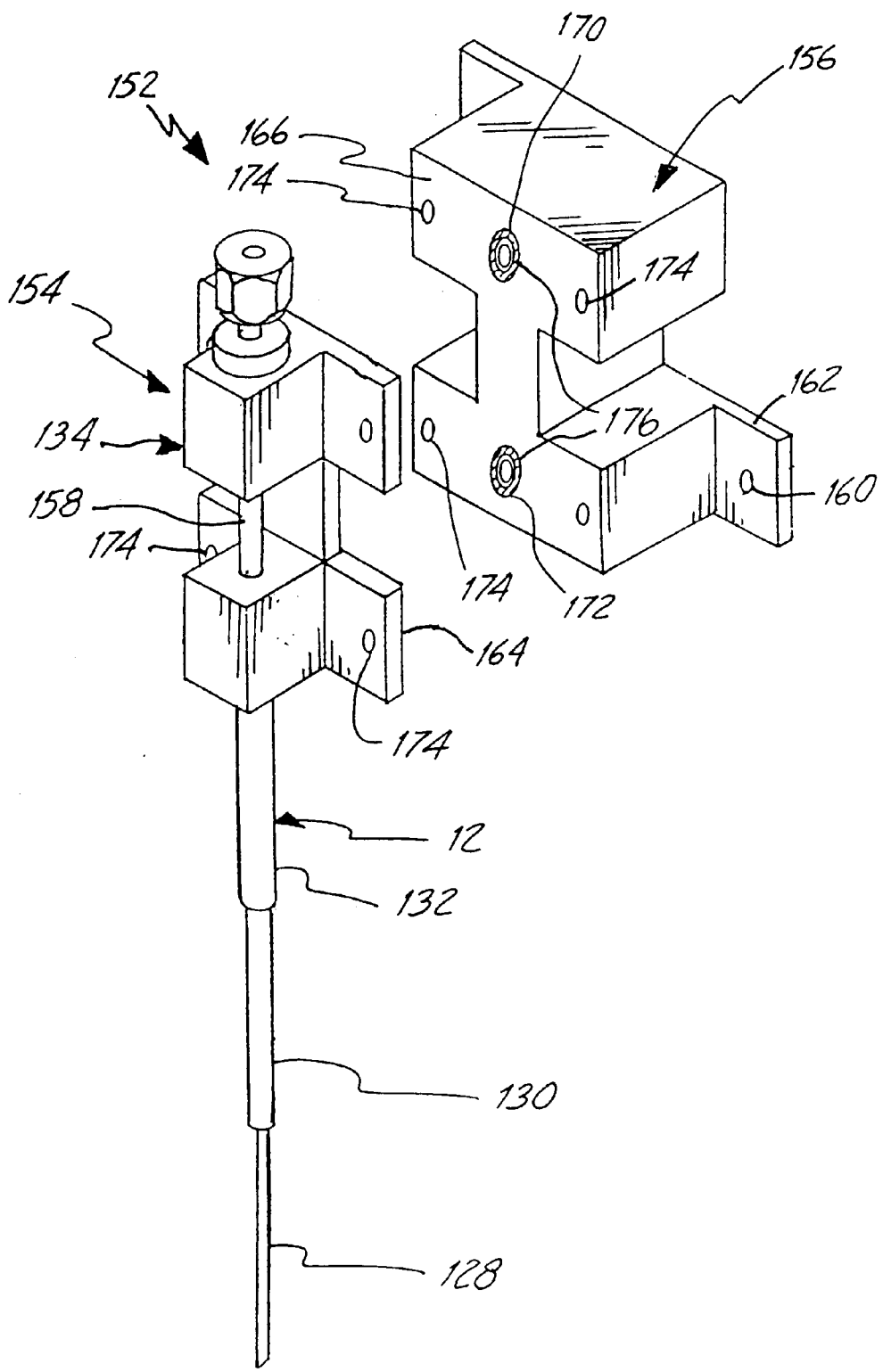
FIG. 9 is a perspective view of a three stage needle in accordance with an embodiment of the invention.

FIG. 9 is a perspective view of needle 12 in accordance with another embodiment of the invention. Here, needle 12 includes a mounting assembly 152, which is adapted to couple needle 12 to autosampler 10 (FIG. 1) One embodiment of mounting assembly 152 includes a needle portion 154 and an autosampler portion 156. Needle portion 154 generally couples to a top portion 158 of needle 12. Autosampler portion 156 is adapted to couple to autosampler 10. This can be accomplished using any suitable fastener, such as a screw that can be inserted through apertures 160 of flanges 162, or by other suitable means. Needle portion 154 includes a mounting face 164 which corresponds to a mounting face 166 of autosampler portion 156. Needle portion 154 and autosampler portion 156 can include apertures 174 which can be used to secure needle portion 154 to autosampler portion 156 and align mounting faces 164 and 166 using a suitable fastener, such as a screw.

Figure 8:
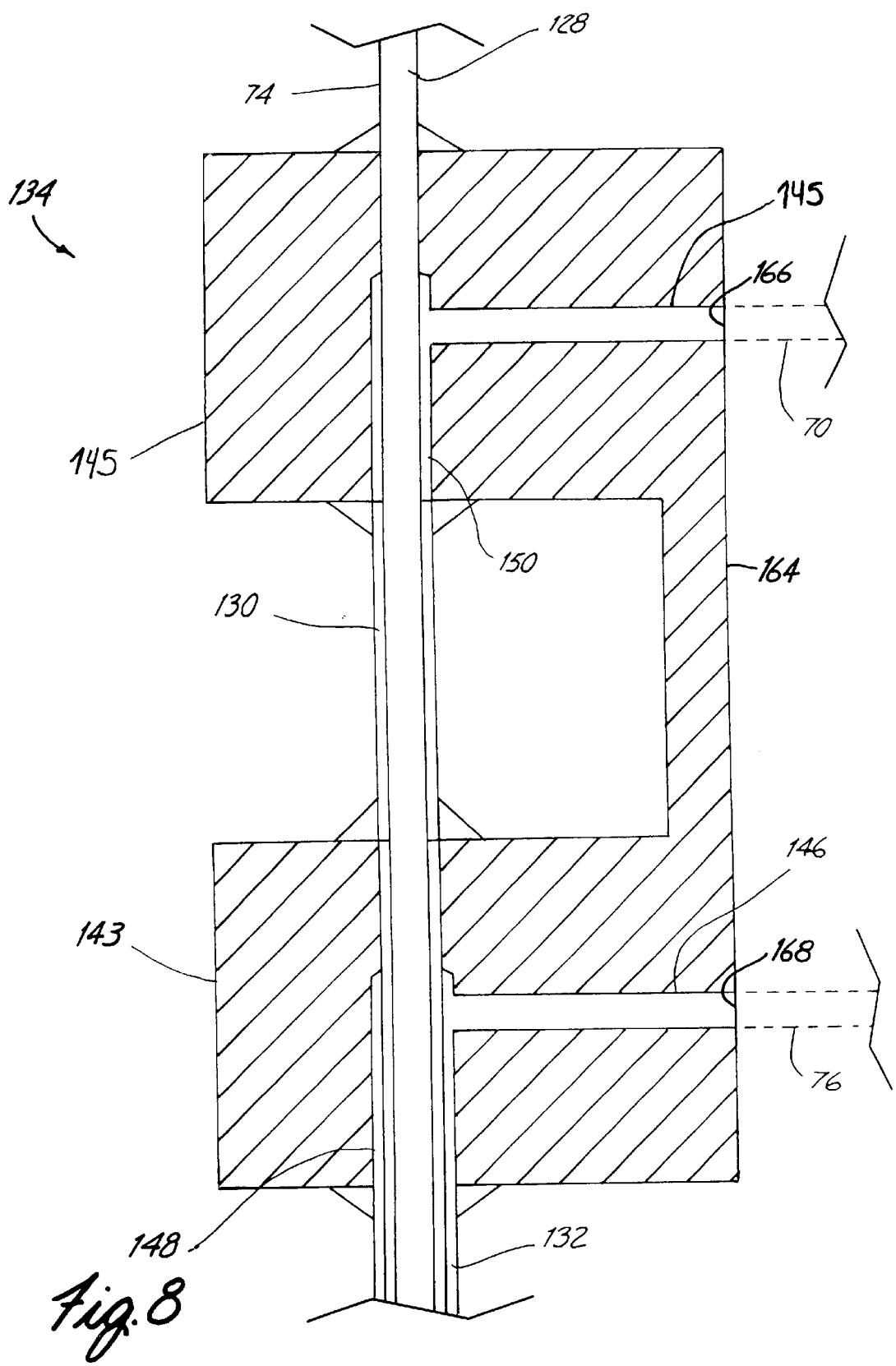
FIG. 8 is a cross-sectional view of a heated block portion of a three stage needle in accordance with one embodiment of the invention.

In one embodiment, needle portion 156 includes the components of heating block 134, shown in FIG. 8, with or without the heating elements (not shown) or heating function of heating block 134. Here, needle portion 154 includes the elements depicted in FIG. 8 including middle stage channel 145 and top stage channel 146, which provide fluidic communication between middle stage 130 and opening 166 of face 164 and top stage 132 and opening 168 of mounting face 164, respectively. Face 166 of autosampler portion 156 includes openings 170 and 172 corresponding to openings 166 and 168 of needle portion 154, respectively. Opening 170 can provide fluidic communication between middle stage 130 and line 70 of sampling station 20 (FIG. 4). Similarly, opening 172 can provide fluidic communication between top stage 132 of needle 12 and line 76 of sampling station 20.

Sealing members 176 can be used to provide leakage protection between mounting face 164 of needle portion 154 and face 166 of autosampler portion 156. Sealing members 176 can be O-rings which are positioned adjacent openings 166 and 168 (FIG. 8) and corresponding openings 170 and 172 of autosampler portion 156. Sealing members 176 are preferably formed of a chemically inert and compressible material such that when needle portion 154 is mounted to autosampler portion 156, sealing members 176 provide the desired leakage protection.

Embodiments of sampling station 20 can perform water sample extractions with multiple standard injections, methanol injections, methanolic dilutions, static headspace extractions, and dynamic headspace extractions using needle 12. All of these procedures can be automated using appropriate control circuitry. Tables I–V list the sequence of operations for conducting the above-mentioned procedures in accordance with various embodiments of the invention. In the operation tables, the individual on-off valves designated by capital letters (A–F) are considered to have two positions: "0" designating off, and "1" designating on, in the table columns. Multi-port valve 64 has common port 0. Only the open port (1–5) will be listed in the operation tables A "--" will be used to indicate that a particular valve position of less importance. The sample extractions performed by sampling station 20 will generally be discussed with reference to a single internal standard line 102, even though several could be used simultaneously as discussed above. As a result, only a single metering valve 108 will be shown in the tables with a "1" indicating that metering valve 108 is in the first position and a "2" indicating that metering valve 108 is in the second position. Additionally, the "vial position" column of the operation tables will indicate whether the vial 24 is up (U) or down (D). When the vial 24 is up (U), the vial 24 is in the raised position where needle 12 is in position to sample the specimen. When the vial 24 is in the down (D) position, needle 12 is not in position to sample the specimen and vial 24 can either be removed from the sampling station or a new vial 24 can be placed in position for sampling.

The examples of sample extraction operations described in Tables I–V each utilize similar procedures for purging and rinsing the stages of needle 12, the various fluid lines, and the syringes of pump 62. These stages can be automated by a control system (not shown). Each of the described rinsing and purging procedures can be repeated as desired. The large syringe 94 can be rinsed by first extracting water from water control module 54 through port 1 of multi-port valve 64 and valve B. Next, the extracted water can be discharged out of large syringe 94 into line 68 through valve B. Finally, the water can be swept through port 4 of multi-port valve 64 to waste by introducing gas through valve A and valve B. Similarly, small syringe 96 can be rinsed with water by extracting water from water control module 54 through port 1 of multi-port valve 64 and sweeping the water through port 4 of multi-port valve 64 to waste with gas.

The stages 128, 130, and 132 of needle 12 can be purged as needed. Typically, bottom stage 128 and middle stage 130 are rinse and purged with water and helium. Water is extracted from water module 54 through port 1 of multi-port valve 64 and valve B using large syringe 94 of pump 62. Bottom stage 128 can be rinsed and purged by expelling water from large syringe 94 into line 68 through valve B and sweeping the water through port 2 of multi-port valve 64, line 74, and bottom stage 128 by introducing helium gas through valves A and B. The discharged water can be collected by vial holder cup 42 and drained to waste. Middle stage 130 can be rinsed and purged by first extracting water from water module 54 using large syringe 94 as described above. Next, water is discharged from large syringe 94 through valve B into line 68. With metering valve 108 in the first position, valve E off, and valve F on, helium is introduced from gas/pressure control module 52 through valves A, B, and port 3 of multi-port valve 64 to flush the contents of line 68, line 70, and line 72 through middle stage 130 of needle 12 and into vial holder cup 42 where the water is drained to waste. Both bottom and middle stages 128, 130 can be purged with only helium if desired. Top stage 132 is generally purged with gas by discharging helium gas from gas/pressure control module 52 through line 66, valve C, line 76, and out top stage 132 of needle 12. Additionally, line 68 connecting valve B to common port 0 of multi-port valve 64 can be rinsed by injecting water from large syringe 94 into line 68 and purging line 68 of its contents by introducing gas through valves A and B and sweeping the contents out port 4 of multi-port valve 64 to waste.

Each of the sampling procedures generally starts at a purge ready state where sampling station 20 waits for a purge ready signal from the concentrator or other analytical instrument indicating that it is ready to receive a sample. In this state the vial is down and valves A, B, C, D, E, and F are closed. The open valve of multi-port valve 64 is unimportant as is the position of metering valve 108.

Table I provides one possible sequence of operations that could be conducted to extract a water sample from a specimen and transfer the specimen along with one or more standards to a concentrator or analytical instrument for analysis. After the standby, rinsing, and purging stages, a vial containing a specimen is presented to needle 12 such that apertures 136 of bottom stage 128 are immersed into the specimen. Large syringe 94 of pump 62 extracts a known volume of the specimen through apertures 136 of bottom stage 128, port 2 of multi-port valve 64, and valve B. Large syringe 94 can be primed by discharging some of the extracted sample through valve B and port 4 of multi-port valve 64 to waste. Standards are introduced to line 70 by selectively actuating the desired metering valves 108 into the second position causing corresponding internal cavities 124 to fill with the desired standard. Metering valves 108 are actuated to their first position and large syringe 94 expels a known quantity of the sample into line 68 through valve B. The sample and standard are flushed with helium gas through valves A, B, port 3 of multi-port valve 64, through metering valves 108 and valve E to the water concentrator or analytical instrument.

TABLE I

Water Sample Extraction

| MODE OF OPERATION | A | B | C | D | E | F | METERING VALVE 108 | MULTI-PORT VALVE 64 | VIAL POSITION |
|---|---|---|---|---|---|---|---|---|---|
| LARGE SYRINGE WATER EXTRACTION | 0 | 1 | 0 | 0 | 0 | 0 | — | 1 | D |
| PURGE LARGE SYRINGE (RINSE) | 1 | 1 | 0 | 0 | 0 | 0 | — | 4 | D |
| LARGE SYRINGE WATER EXTRACTION | 0 | 1 | 0 | 0 | 0 | 0 | — | 1 | D |
| PURGE BOTTOM STAGE | 1 | 1 | 0 | 0 | 0 | 0 | — | 2 | D |
| LARGE SYRINGE WATER EXTRACTION | 0 | 1 | 0 | 0 | 0 | 0 | — | 1 | D |
| PURGE LINES 70 AND 195 | 1 | 1 | 0 | 0 | 0 | 1 | 1 | 3 | D |
| STANDBY AND WAIT FOR PURGE READY | 0 | 0 | 0 | 0 | 0 | 0 | — | — | D |
| RAISE VIAL | 0 | 0 | 1 | 0 | 0 | 0 | — | — | U |
| EXTRACT SAMPLE | 0 | 1 | 1 | 0 | 0 | 0 | — | 2 | U |
| PRIME SYRINGE | 1 | 1 | 1 | 0 | 0 | 0 | — | 4 | U |
| FILL STANDARD(S) | 0 | 0 | 0 | 0 | 0 | 0 | 2 | 3 | U |

TABLE I-continued

Water Sample Extraction

| MODE OF OPERATION | A | B | C | D | E | F | METERING VALVE 108 | MULTI-PORT VALVE 64 | VIAL POSITION |
|---|---|---|---|---|---|---|---|---|---|
| SWEEP SAMPLE AND STANDARD(S) TO WATER CONCENTRATOR | 1 | 1 | 0 | 0 | 1 | 0 | 1 | 3 | U |
| RETURN VIAL TO TRAY | 0 | 0 | 0 | 0 | 0 | 0 | — | — | D |

Alternatively, either large syringe 94 or small syringe 96 can be used to flush the sample and standard through metering valves 108 and valve E to the water concentrator or analytical instrument. If necessary, additional standard injections can be made by repeating the steps of moving the metering valves 108 to the second position to fill the internal cavities 124 with standard, rotating the metering valves 108 to the first position, and sweeping the standards inline 70 to the water concentrator with helium or by expelling a small known amount of sample from large syringe 94 thereby creating a positive pressure flow in the direction of the analytical instrument which in turn "clears" the metering valve. If no further samples are to be extracted, the vial can be returned to the holding tray. Finally, the lines, needle 12, and pump 62 can be purged and rinsed as described above.

of multi-port valve 64. Large syringe 94 can be primed by discharging and sweeping a small amount of the extracted methanol through port 4 of multi-port valve 64 to waste, and line 68 can be rinsed if desired. A known quantity of the methanol is introduced to line 68 and transferred to the vial by sweeping gas through valve A, valve B, port 3 of multi-port valve 64, metering valves 108 (in the first position), valve F, and middle stage 130 of needle 12. With the methanol injection complete, the specimen and methanol can be mixed in the vial 24 as desired. Additional methanol injections can be performed by returning the vial 24 to vial storage area 14, retrieving a new vial 24, and repeating the above-described procedure.

TABLE II

Methanol Injection

| MODE OF OPERATION | A | B | C | D | E | F | METERING VALVE 108 | MULTI-PORT VALVE 64 | VIAL POSITION |
|---|---|---|---|---|---|---|---|---|---|
| LARGE SYRINGE WATER EXTRACTION | 0 | 1 | 0 | 0 | 0 | 0 | — | 1 | D |
| PURGE LARGE SYRINGE (RINSE) | 1 | 1 | 0 | 0 | 0 | 0 | — | 4 | D |
| LARGE SYRINGE WATER EXTRACTION | 0 | 1 | 0 | 0 | 0 | 0 | — | 1 | D |
| PURGE BOTTOM STAGE | 1 | 1 | 0 | 0 | 0 | 0 | — | 2 | D |
| LARGE SYRINGE WATER EXTRACTION | 0 | 1 | 0 | 0 | 0 | 0 | — | 1 | D |
| PURGE MIDDLE STAGE AND METERING VALVES | 1 | 1 | 0 | 0 | 0 | 1 | 1 | 3 | D |
| STANDBY AND WAIT FOR PURGE READY | 0 | 0 | 0 | 0 | 0 | 0 | — | — | D |
| RAISE VIAL | 0 | 0 | 0 | 0 | 0 | 0 | — | — | U |
| EXTRACT METHANOL USING LARGE SYRINGE | 0 | 0 | 0 | 0 | 0 | 0 | — | 5 | U |
| INJECT METHANOL INTO VIAL | 0 | 0 | 0 | 0 | 0 | 1 | 1 | 3 | U |
| EXTRACT SAMPLE WITH SMALL SYRINGE | 0 | 0 | 0 | 0 | 0 | 0 | — | 2 | U |
| LARGE SYRINGE WATER EXTRACTION | 0 | 1 | 0 | 0 | 0 | 0 | — | 1 | D |
| TRANSFER WATER AND SAMPLE TO CONCENTRATOR | 0 | 0 | 0 | 0 | 1 | 0 | 1 | 3 | U |
| RETURN VIAL TO TRAY | 0 | 0 | 0 | 0 | 0 | 0 | — | — | D |

Table II describes a sequence of operations that can be conducted by one embodiment of sampling station 20 to inject a specimen with methanol Prior to injecting the specimen with methanol, bottom stage 128 of needle 12, large syringe 94, small syringe 96, line 70, line 74, and line 68 can be purged or rinsed to remove any possible contaminants using the various methods described above. Next, a vial 24 containing a specimen is presented to sampling station 20. Large syringe 94 extracts a known quantity of the methanol from methanol control module 56 through port 5

One embodiment of sampling station 20 can perform methanolic dilutions on the order of 25 parts methanol to 1000 parts water on specimens that have been previously injected with a suitable volume of methanol, such as by the above embodiment of sampling station 20. After purging and rinsing the various components and lines of sampling station 20 as desired, a known volume of the specimen and methanol is extracted using small syringe 96 through bottom stage 128 of needle 12 and port 2 of multi-port valve 64. Next, large syringe 94 extracts a known volume of water, typically around 5 ml, from water control module 54. Known values of the extracted water (typically 5 ml) and the sample (as little as 5 μl) are then introduced to line 68 and swept through port 3 of multi-port valve 64, valves 108 (in first position), and valve E to the water concentrator for analysis. Finally, the vial can be returned to the vial holder. Additional methanolic dilutions can be conducted by sampling station 20 by retrieving another vial 24 and repeating the above-described procedure.

Large syringe 94 extracts a volume of water from water control module 54. Internal standards system 58 introduces a known quantity of at least one standard to line 70 by the method described above. Large syringe 94 expels a known quantity of water into line 68 through valve B. Helium gas is introduce through valve A, valve B, and port 3 of multi-port valve 64 to sweep the water and standard through valve F and out middle stage 130 of needle 12 to mix with the specimen. Generally, bottom stage 128 is immersed into the specimen and water mixture and middle stage 130 is

TABLE III

Methanolic Sample Extraction & Dilution

| MODE OF OPERATION | A | B | C | D | E | F | METERING VALVE 108 | MULTI-PORT VALVE 64 | VIAL POSITION |
|---|---|---|---|---|---|---|---|---|---|
| LARGE SYRINGE WATER EXTRACTION | 0 | 1 | 0 | 0 | 0 | 0 | — | 1 | D |
| PURGE LARGE SYRINGE (RINSE) | 1 | 1 | 0 | 0 | 0 | 0 | — | 4 | D |
| SMALL SYRINGE WATER EXTRACTION | 0 | 0 | 0 | 0 | 0 | 0 | — | 1 | D |
| PURGE SMALL SYRINGE | 1 | 1 | 0 | 0 | 0 | 0 | — | 4 | D |
| LARGE SYRINGE WATER EXTRACTION | 0 | 1 | 0 | 0 | 0 | 0 | — | 1 | D |
| PURGE BOTTOM STAGE | 1 | 1 | 0 | 0 | 0 | 0 | — | 2 | D |
| LARGE SYRINGE WATER EXTRACTION | 0 | 1 | 0 | 0 | 0 | 0 | — | 1 | D |
| PURGE MIDDLE STAGE AND METERING VALVES | 1 | 1 | 0 | 0 | 0 | 1 | 1 | 3 | D |
| STANDBY AND WAIT FOR PURGE READY | 0 | 0 | 0 | 0 | 0 | 0 | — | — | D |
| RAISE VIAL | 0 | 0 | 0 | 0 | 0 | 0 | — | — | U |
| EXTRACT SAMPLE WITH SMALL SYRINGE | 0 | 0 | 0 | 0 | 0 | 0 | — | 2 | U |
| LARGE SYRINGE WATER EXTRACTION | 0 | 1 | 0 | 0 | 0 | 0 | — | 1 | D |
| TRANSFER WATER AND SAMPLE TO CONCENTRATOR | 0 | 0 | 0 | 0 | 1 | 0 | 1 | 3 | U |
| RETURN VIAL TO TRAY | 0 | 0 | 0 | 0 | 0 | 0 | — | — | D |

Sampling station 20 is also capable of performing both static and dynamic headspace gas extractions. Table IV describes the sequence of operations for performing static headspace extractions and Table V describes a sequence of operations for performing dynamic headspace extractions. Several of the steps are duplicated and will only be described once.

As with the other procedures described above, the components of sampling station 20 are generally purged and rinsed prior to performing the headspace gas extraction. A vial 24 containing a specimen, typically a soil sample, is presented to needle 12 of sampling station 20 after receiving the appropriate signal from the concentrator that it is ready for a sample. In one embodiment, the presented vial can be heated up to approximately 90° C., in the vial holder cup 42.

above the specimen and water mixture. Next, the contents of the vial are agitated using a stir mechanism or other suitable device.

For static headspace extraction (Table IV) the contents of the vial are purged by injecting helium gas through middle stage 130 of needle 12 to flush the headspace gas out top stage 132 of needle 12. This is accomplished by routing the helium from gas/pressure control module 52 through valves A, B, port 3 of multi-port valve 64, valve F, and out aperture 136 of middle stage 130. The headspace gas is exhausted through aperture 136 of top stage 132 by opening valve D. The expelled headspace gas is then sent to a gas chromatograph or other suitable analytical instrument for analysis. Finally, the vial 24 can be returned to the vial holder and the procedure can be repeated if desired.

TABLE IV

Static Headspace Gas Extraction

| MODE OF OPERATION | A | B | C | D | E | F | METERING VALVE 108 | MULTI-PORT VALVE 64 | VIAL POSITION |
|---|---|---|---|---|---|---|---|---|---|
| LARGE SYRINGE WATER EXTRACTION | 0 | 1 | 0 | 0 | 0 | 0 | — | 1 | D |
| PURGE LARGE SYRINGE (RINSE) | 1 | 1 | 0 | 0 | 0 | 0 | — | 4 | D |

TABLE IV-continued

Static Headspace Gas Extraction

| MODE OF OPERATION | A | B | C | D | E | F | METERING VALVE 108 | MULTI-PORT VALVE 64 | VIAL POSITION |
|---|---|---|---|---|---|---|---|---|---|
| LARGE SYRINGE WATER EXTRACTION | 0 | 1 | 0 | 0 | 0 | 0 | — | 1 | D |
| PURGE BOTTOM STAGE | 1 | 1 | 0 | 0 | 0 | 0 | — | 2 | D |
| LARGE SYRINGE WATER EXTRACTION | 0 | 1 | 0 | 0 | 0 | 0 | — | 1 | D |
| PURGE MIDDLE STAGE AND METERING VALVES | 1 | 1 | 0 | 0 | 0 | 1 | 1 | 3 | D |
| STANDY AND WAIT FOR PURGE READY | 0 | 0 | 0 | 0 | 0 | 0 | — | — | D |
| RAISE VIAL | 0 | 0 | 0 | 0 | 0 | 0 | — | — | U |
| LARGE SYRINGE WATER EXTRACTION | 0 | 1 | 0 | 0 | 0 | 0 | — | 1 | D |
| FILL STANDARD(S) | 0 | 0 | 0 | 0 | 0 | 0 | 2 | — | U |
| SWEEP WATER AND STANDARD | 1 | 1 | 0 | 0 | 0 | 1 | 1 | 3 | U |
| INJECT GAS INTO MIDDLE STAGE AND PURGE VIAL OUT TOP STAGE | 1 | 1 | 0 | 1 | 0 | 1 | 1 | 3 | U |
| RETURN VIAL TO TRAY | 0 | 0 | 0 | 0 | 0 | 0 | — | — | D |

For dynamic headspace extraction (Table V) the vial is purged by injecting helium gas through apertures 136 of bottom stage 128 of needle 12 by opening valves A, B, and port 2 of multi-port valve 64. Headspace gas in the vial 24 is then allowed to escape through aperture 136 of top stage 132 of needle 12 and through valve D where it is sent to a gas chromatograph or other suitable analytical instrument for analysis. Finally, the vial 24 can be returned to the vial holder and the procedure can be repeated if desired.

TABLE V

Dynamic Headspace Gas Extraction

| MODE OF OPERATION | A | B | C | D | E | F | METERING VALVE 108 | MULTI-PORT VALVE 64 | VIAL POSITION |
|---|---|---|---|---|---|---|---|---|---|
| LARGE SYRINGE WATER EXTRACTION | 0 | 1 | 0 | 0 | 0 | 0 | — | 1 | D |
| PURGE LARGE SYRINGE (RINSE) | 1 | 1 | 0 | 0 | 0 | 0 | — | 4 | D |
| LARGE SYRINGE WATER EXTRACTION | 0 | 1 | 0 | 0 | 0 | 0 | — | 1 | D |
| PURGE BOTTOM STAGE | 1 | 1 | 0 | 0 | 0 | 0 | — | 2 | D |
| LARGE SYRINGE WATER EXTRACTION | 0 | 1 | 0 | 0 | 0 | 0 | — | 1 | D |
| PURGE MIDDLE STAGE AND METERING VALVES | 1 | 1 | 0 | 0 | 0 | 1 | 1 | 3 | D |
| STANDBY AND WAIT FOR PURGE READY | 0 | 0 | 0 | 0 | 0 | 0 | — | — | D |
| RAISE VIAL | 0 | 0 | 0 | 0 | 0 | 0 | — | — | U |
| LARGE SYRINGE WATER EXTRACTION | 0 | 1 | 0 | 0 | 0 | 0 | — | 1 | D |
| FILL STANDARD(S) | 0 | 0 | 0 | 0 | 0 | 0 | 2 | — | U |
| SWEEP WATER AND STANDARD | 1 | 1 | 0 | 0 | 0 | 1 | 1 | 3 | U |
| INJECT GAS INTO BOTTOM STAGE AND PURGE VIAL OUT TOP STAGE | 1 | 1 | 0 | 1 | 0 | 0 | — | 2 | U |
| RETURN VIAL TO TRAY | 0 | 0 | 0 | 0 | 0 | 0 | — | — | D |

During the above-described headspace gas extractions, heating block 134 can be heated to prevent the condensation of the headspace gas. Typically, heating block 134 is maintained at an elevated temperature of approximately 40–90° C. Similarly, valve D can also be heated to approximately 40–200° C., to prevent headspace gas from condensing during transport to the analytical instrument.

Although the invention has been described with reference to specific embodiments of a water and soil autosampler, workers skilled in the art will recognize that changes can be made in form and detail without departing from the spirit and scope of the invention.

What is claimed is:

1. A needle for use with a sampling station of an autosampler to facilitate gas and liquid extractions of a sample presented to the needle in a vial, the needle comprising:

a bottom stage extendable into a lower portion of the vial and connectable to the sampling station to provide first a fluidic communication path therewith, the bottom stage having at least one aperture;

a middle stage extendable into a middle portion of the vial and connectable to the sampling station to provide a second fluidic communication path therewith, the middle stage having at least one aperture; and a top stage extendable into a top portion of the vial and connectable to the sampling station to provide a third fluidic communication path therewith, the top stage having at least one aperture.

2. The needle of claim 1, wherein the bottom, middle, and top stage are substantially concentric.

3. The needle of claim 1, wherein the top stage surrounds the middle stage and the middle stage surrounds the bottom stage.

4. The needle of claim 1, further comprising a mounting assembly adapted to couple the needle to the autosampler.

5. The needle of claim 4, wherein the mounting assembly includes:

a needle portion coupled to at least one of the bottom stage, the middle stage and the top stage; and an autosampler portion coupled to the autosampler and couplable to the needle portion.

6. The needle of claim 5, wherein:

the needle portion includes:

a middle stage channel in fluidic communication with the middle stage;

a top stage channel in fluidic communication with the top stage; and a first mounting face having openings to the middle and top stage channels; and the autosampler portion includes second mounting face having openings corresponding to the openings of the first mounting face, through which the middle and top stage channels fluidically communicate with the sampling station.

7. The needle of claim 6, wherein the mounting assembly further includes at least one sealing member adapted to provide leakage protection between the first and second mounting faces.

8. The needle of claim 7, wherein the sealing member is an O-ring.

9. The needle of claim 7, wherein sealing members are positioned adjacent the openings of the first end and second mounting faces.

10. The needle of claim 1, further comprising a heating block coupled to at least one of the bottom, middle and top stages, a middle stage channel in fluidic communication with the middle stage, and a top stage channel in fluidic communication with the top stage.

11. The needle of claim 10, wherein the bottom stage extends through the heating block.

12. The needle of claim 10, wherein the heating block further includes a lower heated portion surrounding the top stage channel and an upper heated portion surrounding the middle stage channel.

13. The needle of claim 5, wherein the needle portion includes a heating block.

14. The needle of claim 1, wherein the bottom stage includes a pointed tip.

15. A needle for use with a sampling station of an autosampler to facilitate gas and liquid extractions of a sample presented to the needle in a vial, the needle comprising:

a bottom stage extendable into a lower portion of the vial and connectable to the sampling station to provide a first fluidic communication path therewith, the bottom stage having at least one aperture;

a middle stage extendable into a middle portion of the vial and connectable to the sampling station to provide a second fluidic communication path therewith, the middle stage having at least one aperature;

a top stage extendable into a top portion of the vial and connectable to the sampling station to provide a third fluidic communication path therewith, the top stage having at least one aperture; and a heating block coupled to at least one of the bottom, middle and top stages, a middle stage channel in fluidic communication with the middle stage, and a top stage channel in fluidic communication with the top stage.

16. The needle of claim 15, wherein the bottom stage extends through the heating block.

17. The needle of claim 15, wherein the heating block further includes a lower heated portion surrounding the top stage channel and an upper heated portion surrounding the middle stage channel.

\* \* \* \* \*

UNITED STATES PATENT AND TRADEMARK OFFICE
CERTIFICATE OF CORRECTION

PATENT NO. : 6,706,245 B2
DATED : March 16, 2004
INVENTOR(S) : Neal et al.

It is certified that error appears in the above-identified patent and that said Letters Patent is hereby corrected as shown below:

Column 1,
Line 16, delete "device.," and substitute therefor -- devices --.

Column 6,
Line 12, "(FIG. 1) One" should read -- (FIG 1). One --.
Line 64, "tables A" should read -- tables. A --.

Column 9,
Line 60, "methanol Prior" should read -- methanol. Prior --.

Column 10,
Lines 23-24, delete all but one space between "in" and "the".
Lines 61-62, delete all but one space between "of" and "methanol".

Column 13,
Table IV, fifth entry, delete "STANDY" and substitute therefor -- STANDBY --.

Column 14,
Lines 63-64, delete "first a" and substitute therefor -- a first --.

Signed and Sealed this

Third Day of May, 2005

JON W. DUDAS
*Director of the United States Patent and Trademark Office*